(12) United States Patent
Saito

(10) Patent No.: US 6,340,299 B1
(45) Date of Patent: Jan. 22, 2002

(54) DEVICE FOR POURING DENTAL MIXTURE

(76) Inventor: Yoshiyuki Saito, Towa City Coap Kanaguchi Aoki 702, 9-1, Aoki 5-Chome, Kawaguchi-shi Saitama-ken (JP), 332-0031

( * ) Notice: Subject to any disclaimer, the term of this patent is extended or adjusted under 35 U.S.C. 154(b) by 0 days.

(21) Appl. No.: 09/556,674

(22) Filed: Apr. 21, 2000

(30) Foreign Application Priority Data

Apr. 21, 1999 (JP) .......................................... 11-113766

(51) Int. Cl.[7] .............................................. A61C 13/34
(52) U.S. Cl. ............................ 433/80; 433/86; 222/196
(58) Field of Search ..................... 433/80, 86; 221/200, 221/202; 222/196

(56) References Cited

U.S. PATENT DOCUMENTS

| | | | | |
|---|---|---|---|---|
| 2,526,735 A | * | 10/1950 | Duce | |
| 2,953,282 A | * | 9/1960 | Peterson | |
| 3,898,739 A | * | 8/1975 | Gayso | |
| 4,153,403 A | * | 5/1979 | Schneider | |
| 4,270,675 A | * | 6/1981 | Wicks et al. | 222/196 |
| 5,125,837 A | * | 6/1992 | Warrin et al. | 433/86 |
| 6,139,320 A | * | 10/2000 | Hahn | 433/86 |

FOREIGN PATENT DOCUMENTS

JP            2-131417         11/1990

* cited by examiner

*Primary Examiner*—Ralph A. Lewis
(74) *Attorney, Agent, or Firm*—Jacobson Holman, PLLC

(57) ABSTRACT

The present invention provides a dental-mixture pouring device for pouring a mixture into a target site while minimizing catching of bubbles in the mixture, wherein vibration generated by a vibration generating mechanism 11 is transmitted by vibration transmitting means 17 including a storage section 30 for a mixture 23, and wherein a flexible tip 85 is provided at a terminal portion of the vibration transmitting means 17 for supplying a target site with the mixture 23 flowing out from an orifice 31, 32, 33 of the storage section 30.

8 Claims, 7 Drawing Sheets

FIG. 8
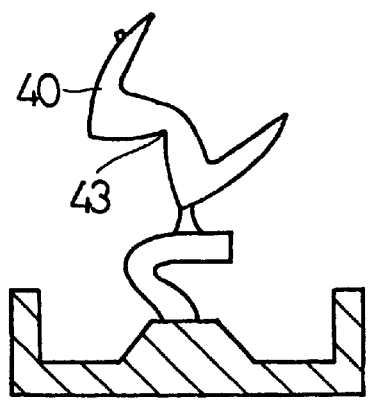
FIG. 9(a)         FIG. 9(b)
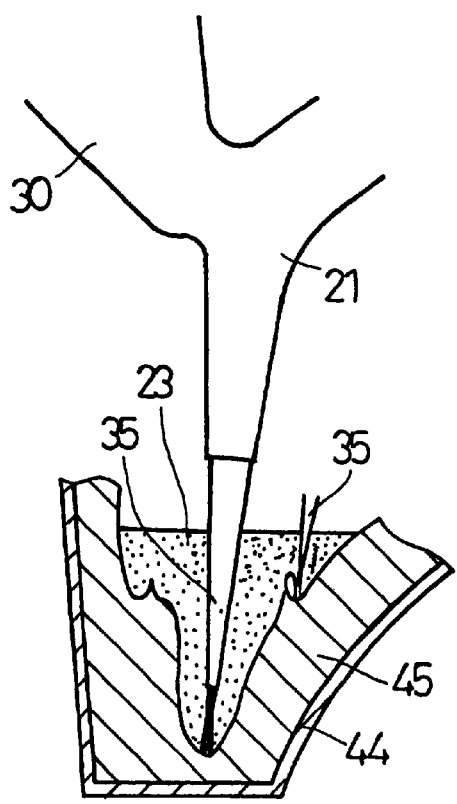 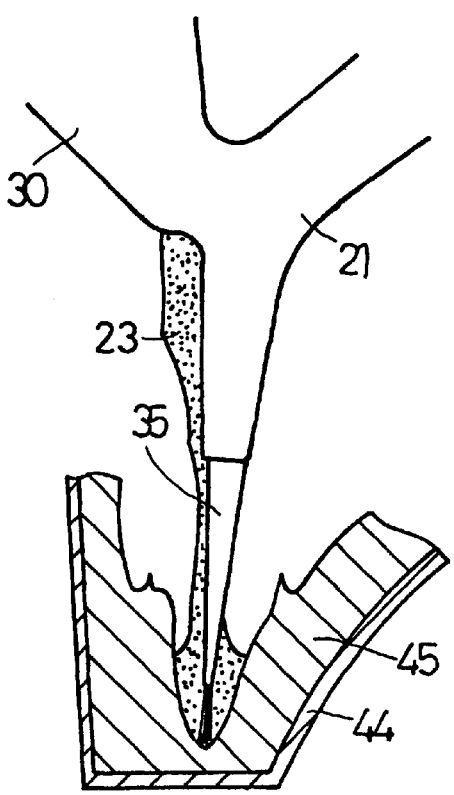

DEVICE FOR POURING DENTAL MIXTURE

FIELD OF THE INVENTION

The present invention relates to a device having a portion that can be held in one hand and which can apply vibration generated by a vibration generating mechanism to a dental mixture in a storage section in order to facilitate pouring of the mixture.

DESCRIPTION OF THE PRIOR ART

In the dental laboratory technique, and operation of pouring a fluid (a mixture) such as a gypsum product or an investment into a restored site such as a crown or inlay in an impression or onto an occlusion or inner surface of a wax pattern is important and significantly affects the quality of a finished product such as denture. Conventionally, a tapered brush, a metallic instrument, or a thin was rod is used to repeat an operation of scooping up a small amount of investment with a tip of the instrument and then pouring it into the target site. Disadvantageously, however, only a small amount of investment can be scooped up at a time and bubbles may be caught in the investment during pouring.

On the contrary, Japanese Utility Model Laid Open No. 2-131417 proposes a device of a dental vibrator. This device is constructed so that a vibrator is vibrated by projecting a tip of a vibrator supported by a base, forward from a tip of a casing and performing a switch operation to engage an intermediate portion of the vibrator with a pinion, which is rotating. According to the description of this device, this construction has such an effect that when a vibrating section at the tip of the vibrator cones in contact with a flowing gypsum product, the gypsum product is vibrated and completely fills an impression.

The vibrator according to the above device, however, must consist of a conductive material because it also acts as part of a switch mechanism. In the specification of the above device, the vibrator is described as a stainless steel rod having a diameter of about 1 mm, and no other example is cited therein.

On the other hand, in producing the impression, its surface must be reproduced very precisely. The material of the impression is generally agar, alginate, or rubber, which is likely to be deformed or damaged under a minor external force. Thus, it can be easily assumed that with the vibrator according to the above device, when a surface of the impression is scratched or rubbed by the tip of the vibrating vibrator, which is made of the stainless steel rod, even a rubber-based impression material, which has a high recoverability, may be deformed or damaged.

The above device does not refer to an operation of bringing the vibrator into contact with the impression surface of the like, but for a thinner impression, it is more difficult to locate the tip portion of the vibrator as deep as possible without bringing it into contact with the impression surface while this portion is buried in the gypsum product. This, the vibrator may actually come in contact with the impression surface. Of course, this possibility is high for an impression surface having a large number of recesses and projections. As a result, with the vibrator of the stainless steel rod as described in the above device, excellent results are not expected because the impression surface is still likely to be deformed or damaged.

The was pattern is more likely to be deformed or damaged under an external force than the impression material, so that delicate operations are required for the burying operation. If the vibrator according to the above device is used for such operations, extremely powerful vibration of the vibrator of the stainless steel rod will pose a problem. Obviously, when the vibrator comes in contact with a surface of the wax pattern, the above vibration may cause a corresponding portion of the surface to be deformed or damaged. Accordingly, due to high risks involved, it is virtually impossible to use the vibrator according to the above device for the burying operation for the wax pattern.

In addition, the amount of gypsum product that can be scooped up by the vibrator of the stainless steel rod according to the above device is substantially equal to that in the above conventional technique, because of no difference between them in form. Consequently, even a small impression cannot be filled during a single operation, whereby an operation of scooping up the gypsum product from a mixer and pouring it into the impression must be repeated a number of times in order to fill a single tooth. As a result, this method may also cause bubbles to be caught in the gypsum product during pouring.

Besides, the vibrator according to the above device also has a problem in terms of removal of bubbles. That is, this vibrator device eliminates bubbles by directly and entirely vibrating a vibrated subject (that is, a gypsum product or the like), but even if bubbles contained in the gypsum product can be eliminated, it is difficult to remove and float, from the impression, bubbles attaching to an inner surface of the impression, particularly, its corners.

Judging from experiences, the mere intense vibration of the gypsum product is not expected to be sufficiently effective in floating bubbles, and a tip of a certain device must be brought into contact with the bubbles to remove them. Of course, the vibrator according to the above device is not suitable as an object to be brought into contact with the bubbles.

Clinically, the inner surface of the impression has a complicated shape with a large number of recesses and projections, and the impression material is thinner in some parts of its surface. In particular, if a rubber-based impression material, which is insufficiently wettable, is used as the impression material, it will be extremely difficult to pour the gypsum product into the impression without generating bubbles. Thus, the prior art must insert a tapered object into the gypsum product to stroke or poke in portions thereof in which bubbles are likely to occur so that the bubbles can be removed and floated from the inner surface of the impression.

SUMMARY OF THE INVENTION

The present invention is provided in view of the above circumstances, and it is an object thereof to enable a flowing dental mixture such as a gypsum product or an investment to be poured into a target site by a small amount at a time until the site is sufficiently filled, and to enable the mixture to be poured into the target site without catching bubbles in the mixture.

It is another object of the present invention to remove, without deforming or damaging an impression surface, bubbles that are caught in the mixture upon pouring into the impression and that remain attached to the impression surface after the pouring.

These and other objects are attained by a device for pouring a dental mixture which is constructed so that vibration generated by a vibration generating mechanism is transmitted by vibration transmitting means including a storage section for the mixture and so that a flexible tip is provided at a terminal portion of the vibration transmitting means for supplying a target site with the mixture flowing out from an orifice of the storage section.

The vibration generating mechanism can be included inside a main body. The above objects can also be achieved by a construction comprising a vibration generating mechanism located outside the main body. In this case, vibration transmitting means having a section that comes in contact with the vibration generating mechanism is used to transmit vibration to the flexible tip.

BRIEF DESCRIPTION OF THE DRAWINGS

FIG. 8 is an explanatory drawing showing a further example of operation in a sectional view; and FIG. 9(a) is an explanatory drawing showing an example of filling of the mixture in a sectional view, and FIG. 9(b) is an explanatory drawing showing how bubbles are removed in a sectional view.

DETAILED DESCRIPTION OF PREFERRED EMBODIMENT

Figure 1:
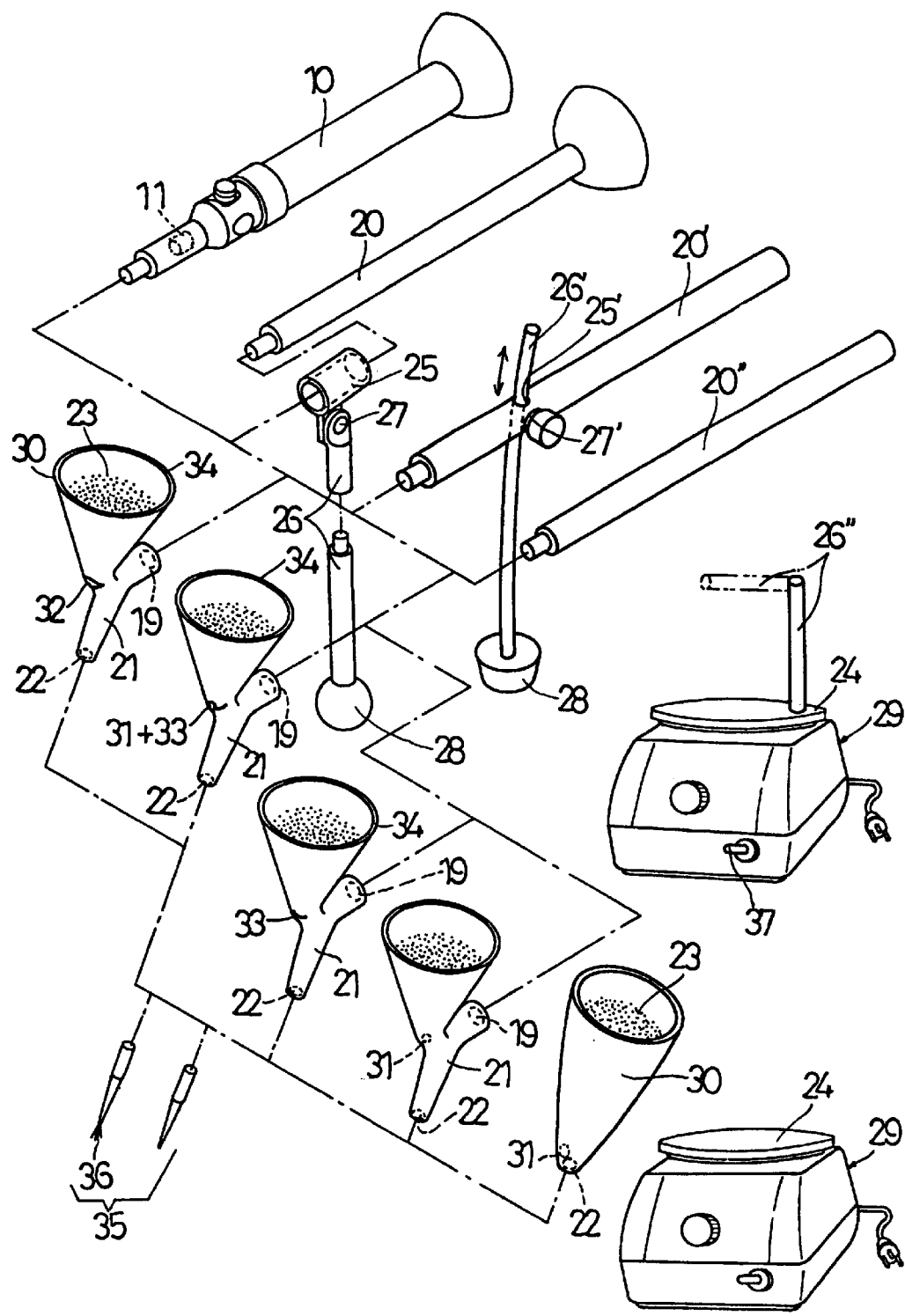
FIG. 1 is an exploded perspective view showing Embodiments 1 and 2 and their Variations 1,2, and 3 of a device for pouring a dental mixture according to the present invention.

A device for pouring a dental mixture according to the present invention is an instrument using a vibration generating mechanism to generate required vibration, thereby facilitating flowing of a dental mixture that fills and impression or the like. The dental mixture, as used herein, collectively refers to dental gypsum products, investments, and refractory model materials.

The device according to the present invention has a section sized and shaped to be held in one hand like a pencil during operation. The vibration generating mechanism available in the present invention is roughly classified into a built-in and a non-built-in types. With either method, the vibration generating mechanism and a flexible tip communicate with each other via vibration transmitting means including a storage section for a mixture so that vibration in the vibration generating mechanism vibrates the mixture in the storage section. On the other hand, if the device has not particular section called a "main body" and a container of the storage section for the mixture acts as a principal section of the vibration transmitting means, the vibration transmitting means comes in contact with the vibration generating mechanism to receive vibration to vibrate the mixture in the storage section.

for the non-built-in type, a desk top vibrator as used in the dental laboratory technique can be used as the vibration generating mechanism. In this case, the vibration transmitting means includes a member for effectively or efficiently transmitting the vibration of the desk top vibrator to the main body. A preferable such member is essentially shaped like a shaft that transmits vibration easily and that is handled easily. The shaft-shaped member refers to a member shaped like an elongate rod or a hollow pipe. The shaft-shaped member is also applicable if the container of the storage section for the mixture acts as the principal section of the vibration transmitting means.

The shaft-shaped member has a higher vibration transmission efficiency when comprised of a hard material, and has a reduced vibration transmission efficiency when comprised of a soft material. The vibration transmission mode varies depending on whether the shaft-shaped member is straight or curved. The present invention assumes both the use of a hard material locking in flexibility and the use of a material having an appropriate flexibility and a high vibration transmission efficiency. With a hard material, the main body and the vibration transmitting means can desirably be connected together using an adjustable method, while with an appropriately flexible material, substantially no operational problem occurs even with a fixed connection method.

To change a manner of transmission effected by the vibration transmitting means, the distance between the vibration generating mechanism and the tip at a terminal of the vibration transmitting means can be adjusted. In addition, an adjustment means can be added for applying lateral movement to the vibration transmitting means, and another adjustment means can be added for applying longitudinal movement to the vibration generating mechanism.

The mixture is flowed out from an orifice formed in the storage section. The orifice may be constantly open so as to maintain a constant opening area, or may have the opening area varied so that the orifice is closed while the device is inoperative and is open while the device is operative. A closable orifice may be provided which is formed like a slit so that its opening is enlarged while the storage section is subjected to a deforming force, whereas the opening is contracted while the storage section is free from the deforming force. In addition, this structure may be a combination of a notch and an opening.

EXAMPLE

Figure 2:
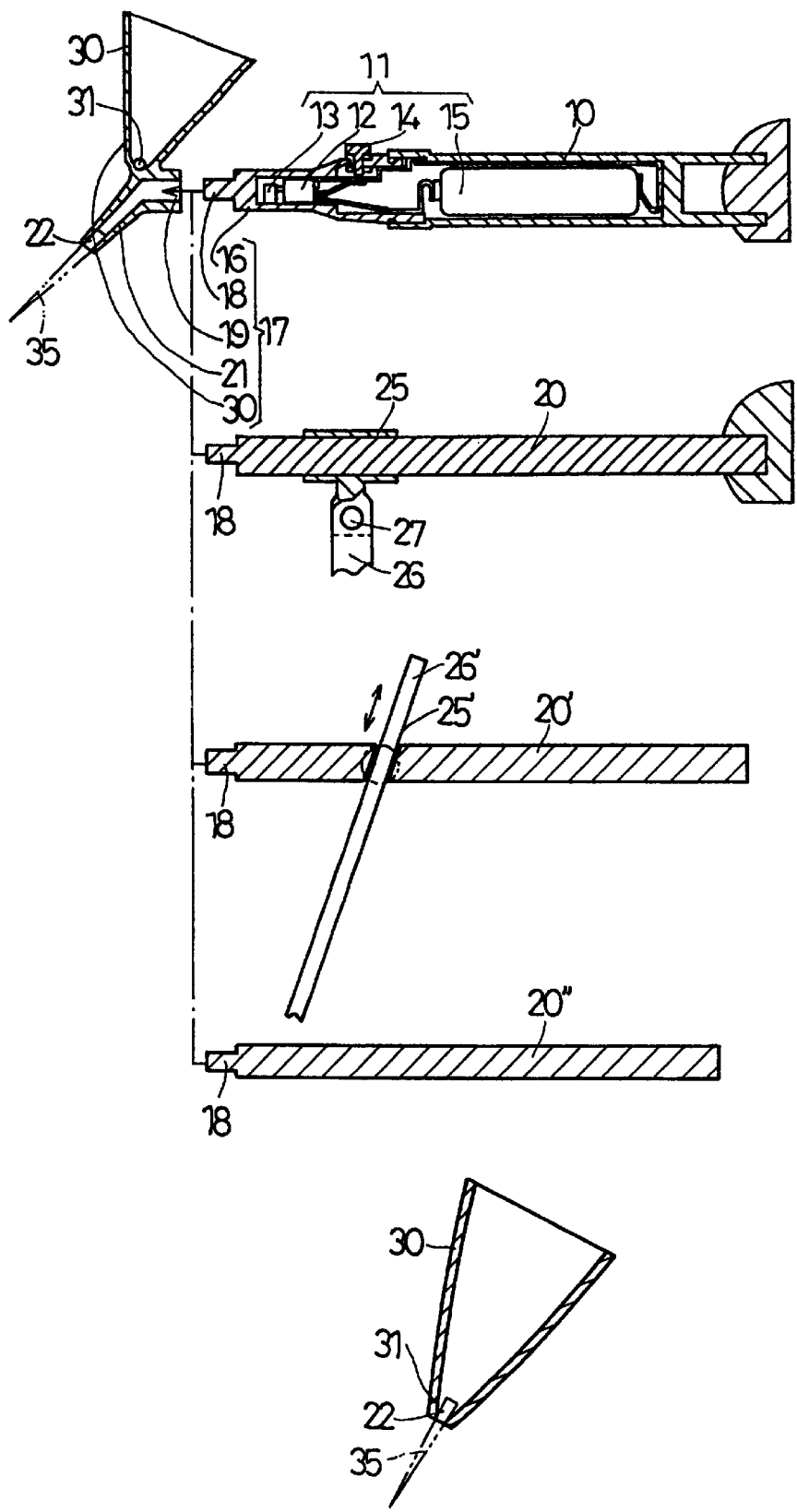
FIG. 2 is a vertical sectional view of the device in FIG. 1.
Figure 3A:
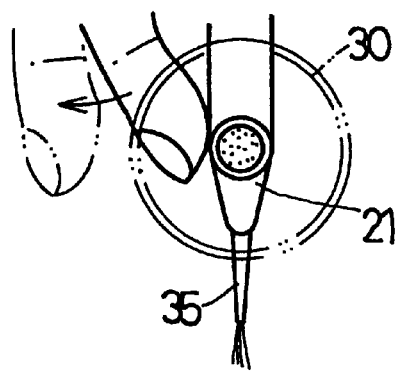
FIG. 3(a) is an explanatory drawing showing how a constantly open orifice is opened and closed.
Figure 3B:
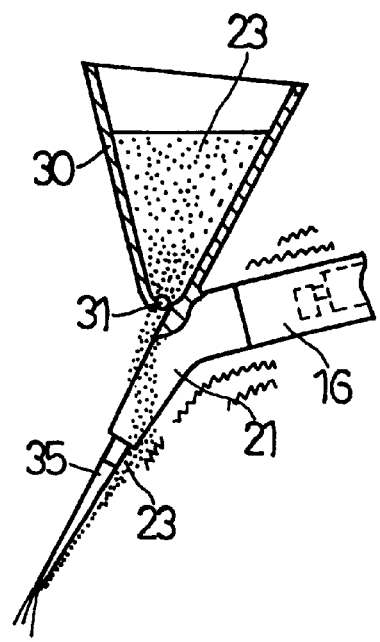
FIG. 3(b) is an explanatory drawing showing how a mixture flows.
Figure 3C:
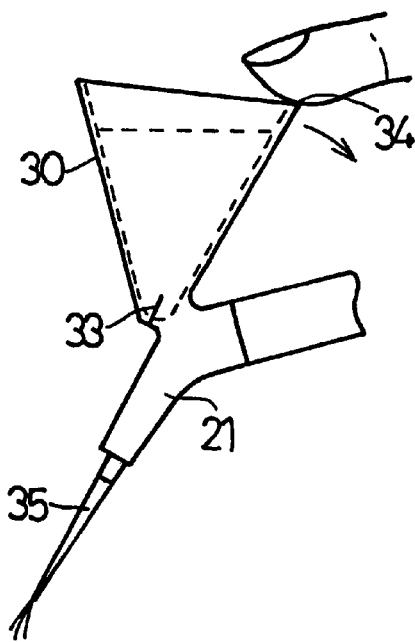
FIG. 3(c) is an explanatory drawing showing how a notch-shaped orifice is opened and closed.
Figure 3D:
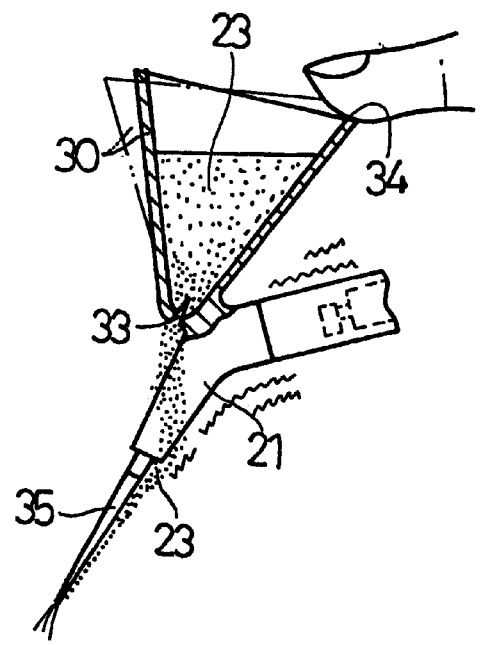
FIG. 3(d) is an explanatory drawing showing how the mixture flows.
Figure 4A:
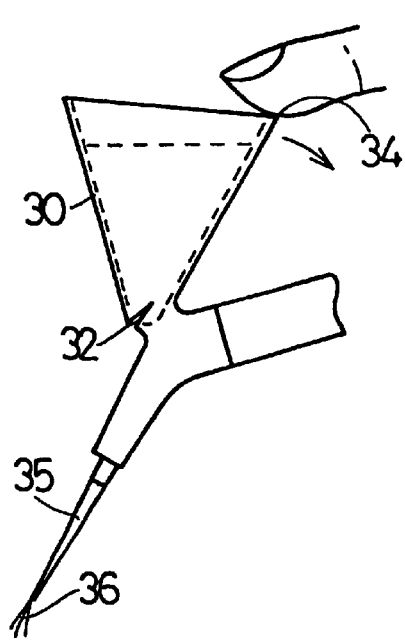
FIG. 4(a) is an explanatory drawing showing how a slit-shaped orifice is opened and closed.
Figure 4B:
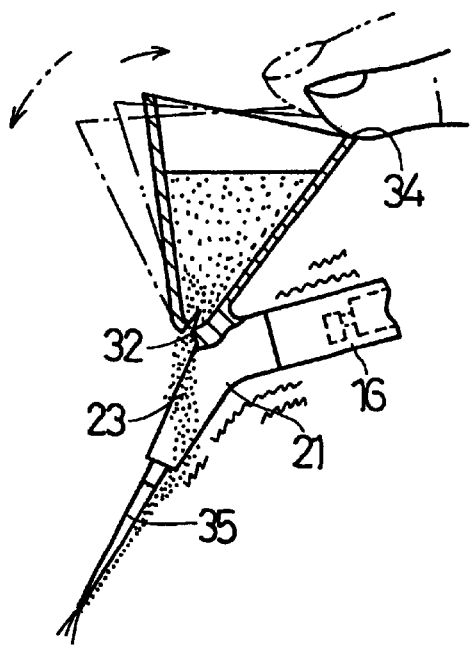
FIG. 4(b) is an explanatory drawing showing how the mixture flows.
Figure 4C:
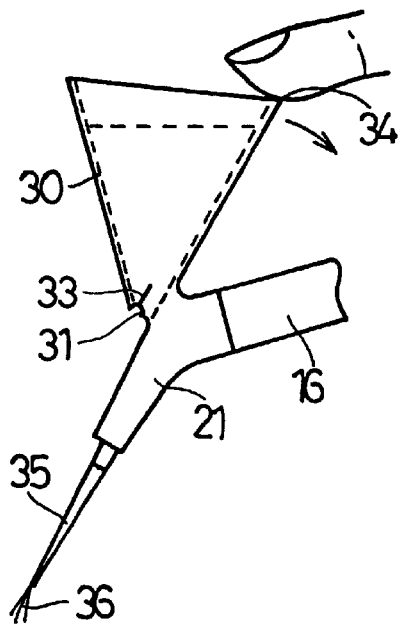
FIG. 4(c) is an explanatory drawing showing how a combination of the notch-shaped orifice and the slit-shaped orifice is opened and closed.
Figure 4D:
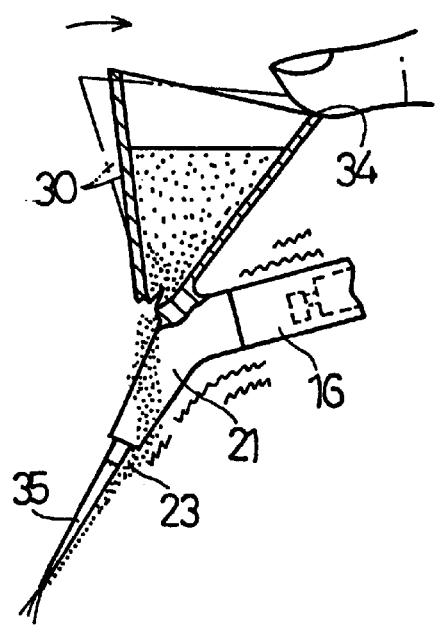
FIG. 4(d) is an explanatory drawing showing how the mixture flows.
Figure 5A:
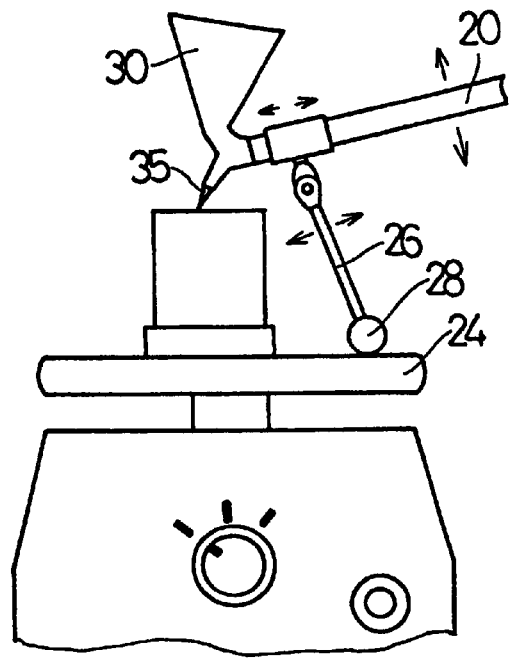
FIG. 5(a) is an explanatory drawing showing the usage of Embodiment 2 in a side view.
Figure 5B:
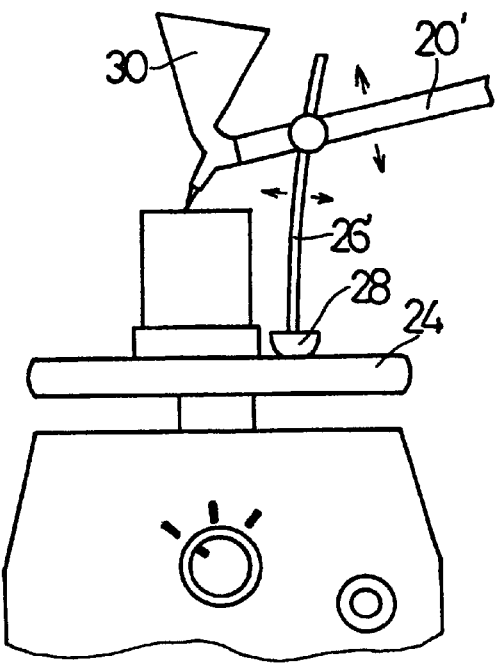
FIG. 5(b) is an explanatory drawing of the usage of Variation 1 in a side view.
Figure 5C:
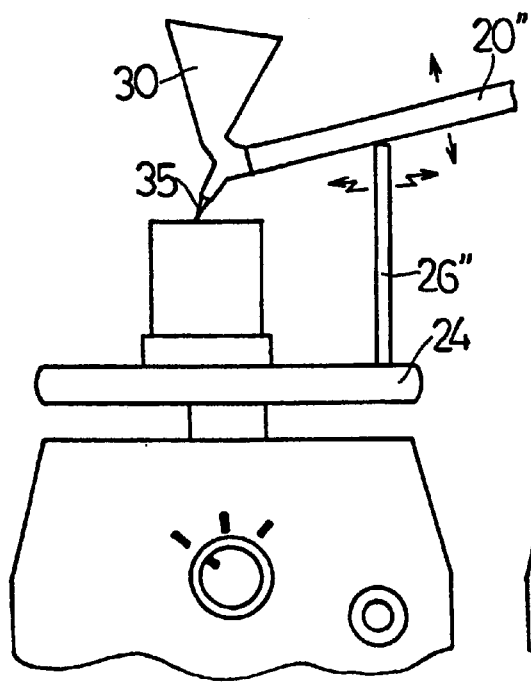
FIG. 5(c) is an explanatory drawing of the usage of Variation 2 in a side view.
Figure 5D:
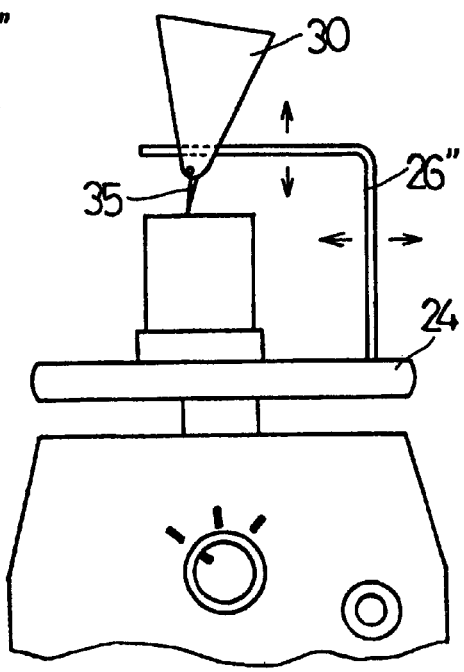
FIG. 5(d) is an explanatory drawing of the usage of Variation 3 in a side view.

The present invention will be described below in detail with reference to the illustrated embodiments. FIGS. 1 and 2 show a main body 10 having a built-in vibration generating mechanism 11, each example having a main body 20 used with a non-built-in vibration generating mechanism 24, and an example in which a container of a storage section constitutes a principal part of the vibration transmitting means. In addition, in a storage section 30 for a mixture 23 are shown a constant orifice 31 that is constantly open, a slit-shaped orifice 32 that is open to the extent that the mixture does not flow out naturally but that can have the numerical aperture varied, a closable notch-shaped orifice 33, and an example of a combination of the constant orifice 31 and the notch-shaped orifice 33.

Embodiment 1 having the built-in vibration generating mechanism 11 will be explained, A drive source 12 for the vibration generating mechanism 11 is located near a tip portion of the hollow main body 10, and a rotating shaft of the vibration generating mechanism 11 includes an eccentric weight 18. In the illustrated Embodiment 1, the drive source 12 is comprised of a micro motor particularly suitable for the present invention, for turning on and off power from a power supply 15 based on operation of a switch 14. According to the embodiment, all mechanisms are incorporated in the main body. The power supply 15, however, need not be a battery but may be externally exposed using a cord.

The illustrated example is constructed to transmit vibration of the eccentric weight 28 which is effected by the drive source 12, comprised of a micro motor, to the mixture in the storage section 30 while minimising the amount of vibration absorbed by the main body 10. In this construction, the motor, which is the drive source, is housed and fixed in a hollow drive section 16. The main body 10 is hard and is significantly deflected (amplifies vibration) when vibrated by the vibration generating Mechanism 11.

Amplification of vibration can be adjusted by moving the position of the motor. For example, the amplitude of the vibrating section 16 decreases the distance between the motor and a central portion of the main body, while the amplitude increases as the motor is located further from the central portion. Thus, appropriate selection of the motor position enables the amplitude to be adjusted and optimally set for transmission to the vibration transmitting means 17 without allowing vibration originating in the motor to be absorbed by the main body 10.

The vibration transmitting means 17 is constructed to transmit vibration generated by the vibration generating mechanism 11 to a flexible tip 85. In Embodiment 1, the vibration transmitting means 17 consists of a main body top portion 18, a connection target thereof 19, a connection member 21 having the connection target 19 formed at one end, and the storage section 80 integrally formed on the connection member 21. Another end of the connection member 21 constitutes a connection target section 22 connecting to the flexible tip.

The storage section 30 can be comprised, for example, of a cup- or corn-shaped member sized and shaped equivalently to a container filled with an investment or the like, in order to store a sufficient amount of mixture 23 such as a gypsum product to fill several tooth.

Embodiment 2 having a non-built-in vibration generating member 24 will be described. The vibration generating mechanism 24 can be comprised of a diaphragm of a desk top vibrator 29 for the dental laboratory technique. In the illustrated Embodiment 2, the main body 20 is shaped like a rod, which can be held in one hand for operation similarly to the built-in type, wherein a shaft-shaped member 26 acting as part of the vibration transmitting means 17 is journaled at its upper end to slide mains 25 of a uniform thickness which is attached to the main body on its outer periphery.

The slide mains 25 is oscillated in a longitudinal direction of the main body 20 to adjust the distance between the vibration generating means 24 and the storage section 30 for the mixture and thus the intensity of vibration. Instead of the slide means 25, a plurality of holes can be formed in a longitudinal direction of the main body 20 so as to allow selection of one of the holes in which an upper end of the shaft-shaped member is fitted, thereby enabling the above distance to be adjusted (not shown).

in the drawing, reference numeral 27 designates a support shaft journaling the vibration transmitting means 17 to the slide means 25 so that the vibration transmitting means 17 can be rotated around the support shaft 27 in the longitudinal direction. The support shaft 27 section may be adapted for tightening. Reference numeral 28 denotes a mass provided as a non-slip at a lower end of the shaft-shaped member 26, which is part of the vibration transmitting means 17. The mass 28 can receive substantially the same vibration in every orientation however it is brought into contact with the vibration generating mechanism 24. The shaft-shaped member 26 in the example includes a detachable connection section in the middle.

A hole can be formed in a main body 20' as slide means 25' so that a shaft-shaped member 26' can be removably inserted into the hole and locked at an arbitrary position by means of a support shaft 27'. This is shown as variation 1 of embodiment 2, which has the second main body 20' from the right edge of FIG. 1.

A method for providing a shaft-shaped member 26" on the vibration generating mechanism 24 side is also shown as Variation 2 Embodiment 2, which has a rod-shaped main body. This corresponds to a main body 20" at the right end in FIG. 1. The shaft-shaped member 26" may include an arm-shaped section to facilitate contact with the vibration generating mechanism.

As in Embodiment 1, the main body 20 in Embodiment 2 and Variations 1 and 2 has connection means provided at its tip to connect to the storage section 30 for the mixture. Accordingly, detailed description thereof is omitted. The vibration transmitting means 17 in Embodiment 2 consists of the vibration generating mechanism 24, the shaft-shaped member 26, the main body 20, its tip portion 18 and connection target 19, and the connection member 21 having the storage section 30.

As an alternative to the non-built-in type, Variation 3 will be explained. This variation consists substantially only of the storage section 30. In the storage section 30 for the mixture 23, the container acts directly as part of the vibration transmitting means 17 so that vibration generated by the vibration generating mechanism 24 is transmitted to the storage section 30 directly or via the shaft-shaped member 26", which is used for transmitting vibration.

The storage section 30 may have the orifice 33 having a constant or variable opening area, as described above. The latter construction, however, becomes complicated if a mechanical structure is used for opening and closing. Thus, according to this embodiment, the container, acting as the storage section 30, is formed of an elastically deformable synthetic resin material and a slit-shaped orifice 31 and a notch-shaped orifice 32 are formed at a bottom portion of the storage section 30 to open and close the storage section 30. An appropriate material of the storage section 30 is a synthetic resin, rubber, or the like having adequate hardness and flexibility for obtaining a high recovery force.

The orifices 31, 32, 33 are formed in the bottom portion of the storage section 30 or in its neighborhood. Desirable, the storage section 30 is generally shaped like a corn, and a narrow pointed bottom portion thereof allows fine flow adjustments more easily than a wide bottom portion thereof. See FIGS. 3 and 4. For flow adjustments or opening and closing operations, the constantly opened orifice 31 is opened and closed by the fingers and the slit- and notch-shaped orifices 32, 33 are opened and closed by applying a deforming force to the storage section 30 in a manner pushing it open. Thus, a top portion of the storage section 30 constitutes and operation section 34.

Even when submitted to vibration, the notch-shaped orifice 33 remains closed unless it is opened by pushing the operation section 34. Accordingly, bubbles can be easily controlled simply by vibrating the mixture 23; this bubble control, in combination with the variable adjustments of the flow, allows pouring of the mixture to be completed in a shorter time.

A tip 35 is located at a terminal of the vibration transmitting system for enabling the mixture 28 flowing out from the storage section 30 to be vibrated for supply to a target site. The tip 35 transmits further downward the mixture 23 transmitted through the vibration transmitting system. Structurally, the tip 85 must have a relatively elongate form having a function of appropriately cushioning vibration generated by and transmitted from the vibration generating mechanism 11, 24 and having flexibility so as not to be deformed or damaged upon coming in contact with the target site such as an impression.

In the illustrated embodiment, the tip 35 is removably fitted in the connection target section 22 at the terminal of the storage section 30. Several types of chips 35 are provided so that an optimal tip can be used for the operation. Important properties required for the tip 35 are a cushioning effect and flexibility, as described above. The point of a brush, which is shaped like the tip of an ear, is best for the cushioning effect. I should be noted, however, that an excessively long brush point may cause the vibration of the entire tip to be weakened to increase the amount of air remaining in the brush.

Next, the operation of the device for pouring a dental mixture according to the present invention will be described in conjunction with its usage.

Next, the operation of the device for pouring a dental mixture according to the present invention will be described in conjunction with its usage.

First, the dental mixture 23 such as a mixed investment is scooped up using a spatula or the like and is stored in the storage section 30. Then, the main body 10, 20, 20', 20" or the storage section 30 is held in the hand. Then, in embodiment 1, the switch 14 is depressed to actuate the vibration generating mechanism 11, while the point of the tip 85 is immersed in the above investment or the like. The mixture 23 in the storage section 30 is vibrated under vibration transmitted from the vibration transmitting means 17. Then the orifice 31 to 33 is opened, air can be removed even from the brush point 36 at the point of the tip 35. In Embodiment 2, a switch 37 for the vibrator 29 is turned on, and an end of the vibration transmitting means 17 is abutted on the vibration generating mechanism 24 so as to transmit vibration to the storage section 30 for an operation similar to that described above.

If the storage section 30 has the orifice 32, 33 that variably adjusts the flow of the mixture 19, the operation section 34 is pushed to open the slit or notch in order to adjust the outflow. In this case, not only the orifice 32, 33 can be opened and closed but its opening area can also be increased and reduced easily. In addition, to stop the outflow, the slit-shaped shaped orifice 32 or the notch-shaped orifice 33 can be closed by releasing the finger from the operation section 84 to allow it to recover by means of elasticity. The outflow of the mixture 23 can also be adjusted by increasing or reducing the intensity of vibration transmitted from the vibration generating mechanism 11, 21 to the storage section 30.

FIG. 5 shows examples of usage in Embodiment 2 and its Variations of the present invention. Embodiment 2 in FIG. 5(a) has the slide means 25 sliding in the axial direction of the main body, wherein the mass 28 at the lower end of the shaft-shaped member 26 is abutted on the vibration generating mechanism 24 to receive and transmit vibration to the tip 35 by the vibration transmitting means 17. Variation 1 in FIG. 5(b) is substantially the same as Embodiment 2 except that the slide means 25' changes not only its position on the main body but also the connection position of the shaft-shaped member 26'. Variation 2 in FIG. 5(c) shows the usage where vibration is received by abutting the main body 20" on the shaft-shaped member 26" installed on the vibration generating mechanism 24 in a fashion extending in a vertical direction of the device. Variation 3 in FIG. 5(d) has no rod-shaped main body. In this example, vibration is applied by abutting the outer surface of the container of the storage section 30 directly on the shaft-shaped member 26" installed on the vibration generating mechanism 24 in a manner extending therefrom in the vertical direction. In Embodiment 2 and each Variation, the adjustment of the outflow of he mixture 23 is the same as described in the above Embodiment 1.

Figure 6:
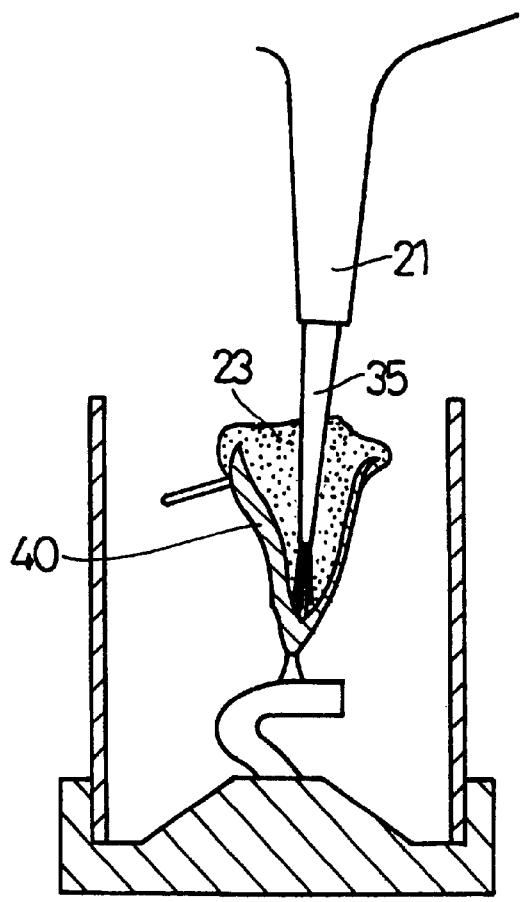
FIG. 6 is an explanatory drawing showing an example of operation in a sectional view.
Figure 7A:
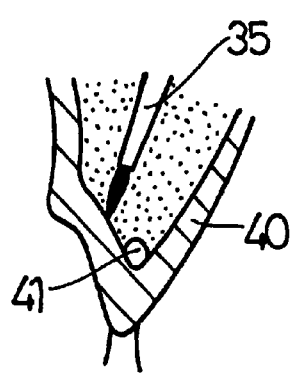
FIG. 7(a) is a sectional view showing an example of a bubble remaining site.
Figure 7B:
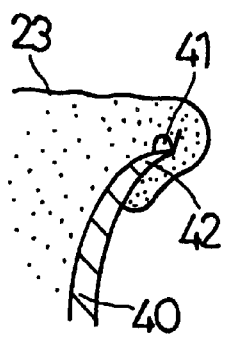
FIG. 7(b) is a sectional view showing another example of a bubble remaining site.

When this device is used to pour the investment onto, for example, and inner surface of a wax pattern of a cast crown, the point of the tip is brought into contact only with the deepest portion of the wax pattern but not with said surfaces of the inner surface thereof while the tip is not vibrated, as shown in FIG. 6. Then, when the tip is vibrated, the investment, which is the mixture 23, flows down continuously to the point of the tip to fill the wax pattern 40 with the investment starting from the deepest portion. At the same time, portions of the inner surface of the wax pattern 40 in which bubbles 41 are likely to occur are stroked (see FIG. 7(a)). These operations are performed until the investment 23 starts to overflow a margin section 42 of the wax pattern 40 in which the bubble 41 is apt to occur (FIG. 7(b)). Subsequently, the point of the tip is drawn out from the investment 23.

Repeating the above operations enables the wax pattern 40 to be filled with the investment (28) easily without mixing bubbles thereinto even if a plurality of wax patterns 40 are used. In addition, for a site 43 such as an occlusion surface of the wax pattern which has a large recess or projection (FIG. 8), the investment (23) can be poured in the wax pattern without the mixture of bubbles by bringing the point of the tip 35 into contact with the occlusion surface and then vibrate the tip to spread the investment.

An operation of pouring a gypsum product onto an inner surface of an impression is essentially similar to the operation of pouring the investment onto the inner surface of the cast crown pattern. The gypsum product, the mixture 28, fills on the inner surface of the impression, which is formed of an impression material 45 in a tray 44, and in this case, the tip 35 is located in the deepest portion of the impression before vibration, thereby ensuring the guidance of the gypsum product.

As described above, the remaining bubble 41 can be floated by using the flexible point of the tip 35 to stroke the inner surface to bring the vibrating tip point into direct contract with the bubble 41. In Embodiment 1, the operation of pouring the mixture 28 according to the present invention enables the pouring without vibration on a table, as required in prior art devices. In addition, since the mixture 28 such as an investment or a gypsum product is vibrated within the storage 30, hardening is delayed to provide time to spare for the operation.

Since the present invention is constructed and operated as described above, the dental mixture can be continuously poured into a target site such as the deepest portion of the inner surface of the impression, by a small amount at a time until the impression is fully filled with the mixture, thereby preventing bubbles from being caught in the mixture. For remaining bubbles, the flexible tip is brought into contact with the target site to remove the bubbles from the inner surface of the impression in such a manner as to directly lift them, whereby the bubbles are effectively removed to prevent the impression surface from being deformed or damaged. In particular, the present invention provides the following significant effect: like the main body with the built-in vibration generating mechanism, the main body without it can efficiently transmit vibration to the storage section; this efficient transmission, in combination with the flow varying construction that does not allow the orifice to be opened simply by means of vibration transmission, enables significantly easy operations.

What is claimed is:

1. A device for pouring a dental mixture having a portion that can be held in one hand, said device comprising:

a main body having a terminal end;

a vibration generating mechanism positioned near said main body for generating vibration to the dental mixture;

a storage section, connected to said main body and in communication with said vibration generating mechanism through said main body, for receiving and storing the dental mixture in order to facilitate pouring of the mixture, said storage section having an orifice, said orifice for permitting the mixture from flowing out the storage section;

vibration transmitting means having a terminal portion and for transmitting vibrations generated from said vibration generating mechanism to said storage section for the mixture; and a removable and flexible tip positioned below the orifice for supplying a target for the mixture flowing out the orifice of the storage section.

2. The device for pouring a dental mixture according to claim 1, wherein said main body being hollow and said vibration generating mechanism being positioned inside said hollow main body, wherein vibration generated by the vibration generating mechanism is transmitted to said flexible tip by means of the vibration transmitting means.

3. The device for pouring a dental mixture according to claim 1, wherein said vibration generating mechanism being located outside said main body, wherein the vibration transmitting means is provided to transmit vibration to said flexible tip through a contact with the vibration generating mechanism.

4. The device for pouring a dental mixture according to claim 3, wherein said vibration transmitting means including slide means for enabling adjustments of said vibration transmitting means thereof attached to the main body.

5. The device for pouring a dental mixture according to claim 3, wherein said vibration transmitting means includes a support shaft journaled thereto at said main body for rotation in a longitudinal direction of the device.

6. The device for pouring a dental mixture according to claim 1, wherein said orifice is enlarged when a deforming force is applied, the orifice is contracted or closed when no deforming force is applied.

7. The device for pouring a dental mixture according to claim 1, wherein said orifice is a slit formed in an elastically deformable storage section for opening and closing.

8. The device for pouring a dental mixture according to claim 1, wherein said orifice has a notch formed in an electrically deformable storage section for opening and closing.

* * * * *